United States Patent [19]

Buchholz et al.

[11] Patent Number: 5,493,442
[45] Date of Patent: Feb. 20, 1996

[54] METHOD FOR REALIZING A FILTER EDGE, OPTICAL THIN-FILM AND OPTICAL DEVICE WITH SUCH A FILM

[75] Inventors: Jürgen Buchholz, Sevelen, Switzerland; Peter Wierer, Bludenz, Austria

[73] Assignee: Balzers Aktiengellschaft, Balzers, Liechtenstein

[21] Appl. No.: 218,736

[22] Filed: Mar. 28, 1994

[30] Foreign Application Priority Data

Apr. 2, 1993 [CH] Switzerland .................. 1025/93

[51] Int. Cl.⁶ ..................................... G02B 5/28
[52] U.S. Cl. ................ 359/359; 359/361; 359/589; 359/885; 359/586; 428/426
[58] Field of Search .................... 359/359, 360, 359/586, 589, 588, 885, 361; 428/426

[56] References Cited

U.S. PATENT DOCUMENTS

| | | | |
|---|---|---|---|
| 4,909,254 | 3/1990 | Wilkinson | 359/359 |
| 4,940,636 | 7/1990 | Brock et al. | 359/586 |
| 5,085,926 | 2/1992 | Iida et al. | 359/359 |
| 5,103,337 | 4/1992 | Schrenk et al. | 359/359 |
| 5,140,457 | 8/1992 | Letter | 359/359 |
| 5,157,547 | 10/1992 | Paesold | 359/586 |

*Primary Examiner*—Paul M. Dzierzynski
*Assistant Examiner*—Audrey Chang
*Attorney, Agent, or Firm*—Notaro & Michalos

[57] ABSTRACT

In order to reduce the number of thin-films necessary to construe an interference band-pass filter for exclusive transmission of light in the UVA range the filter edge towards smaller wavelengths in the spectral characteristic is realized by the absorption edge of the material of one of the thin-films of a thin-film interference filter which filter produces the band-pass filter edge directed towards higher wavelengths.

58 Claims, 11 Drawing Sheets

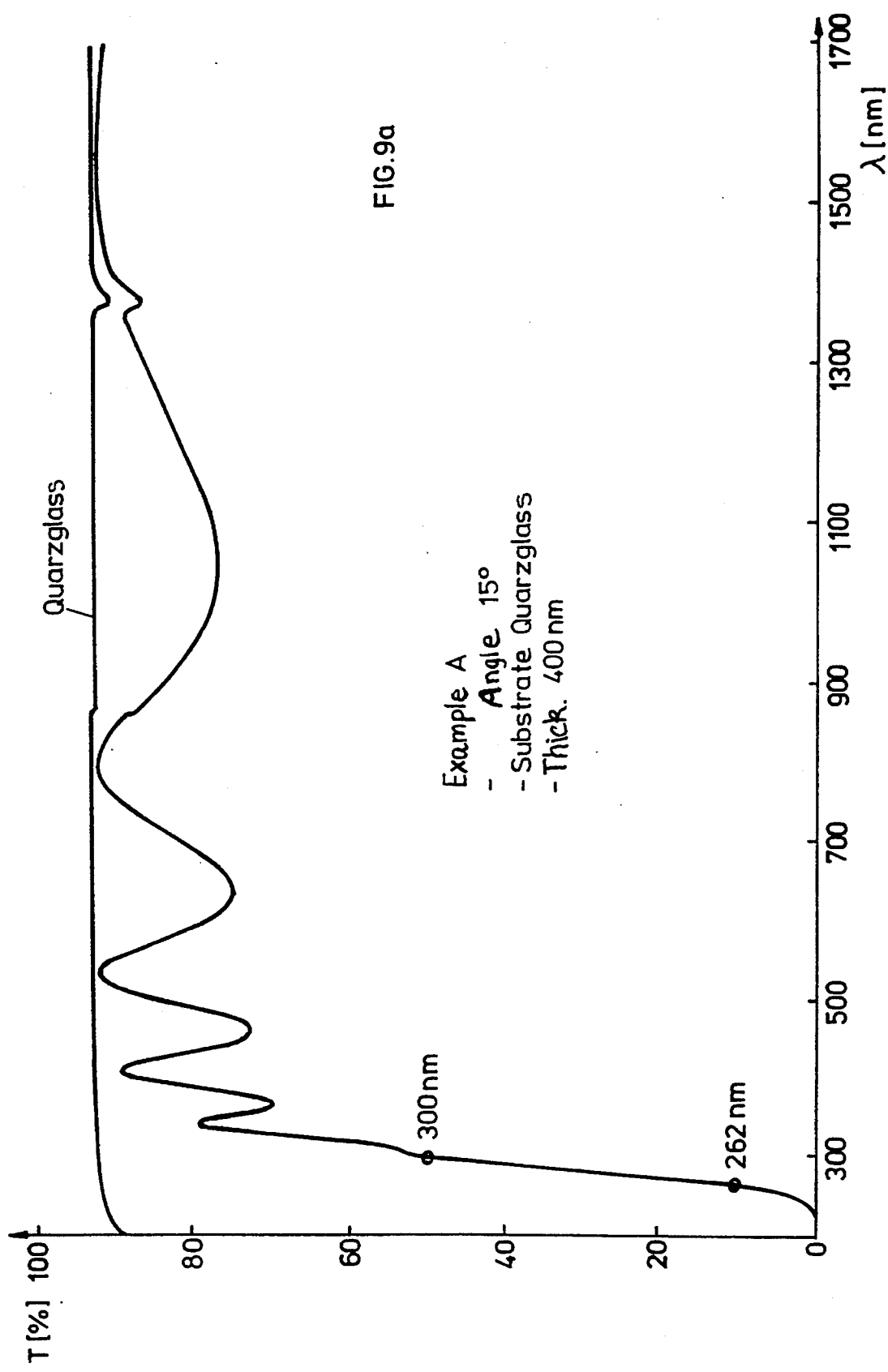

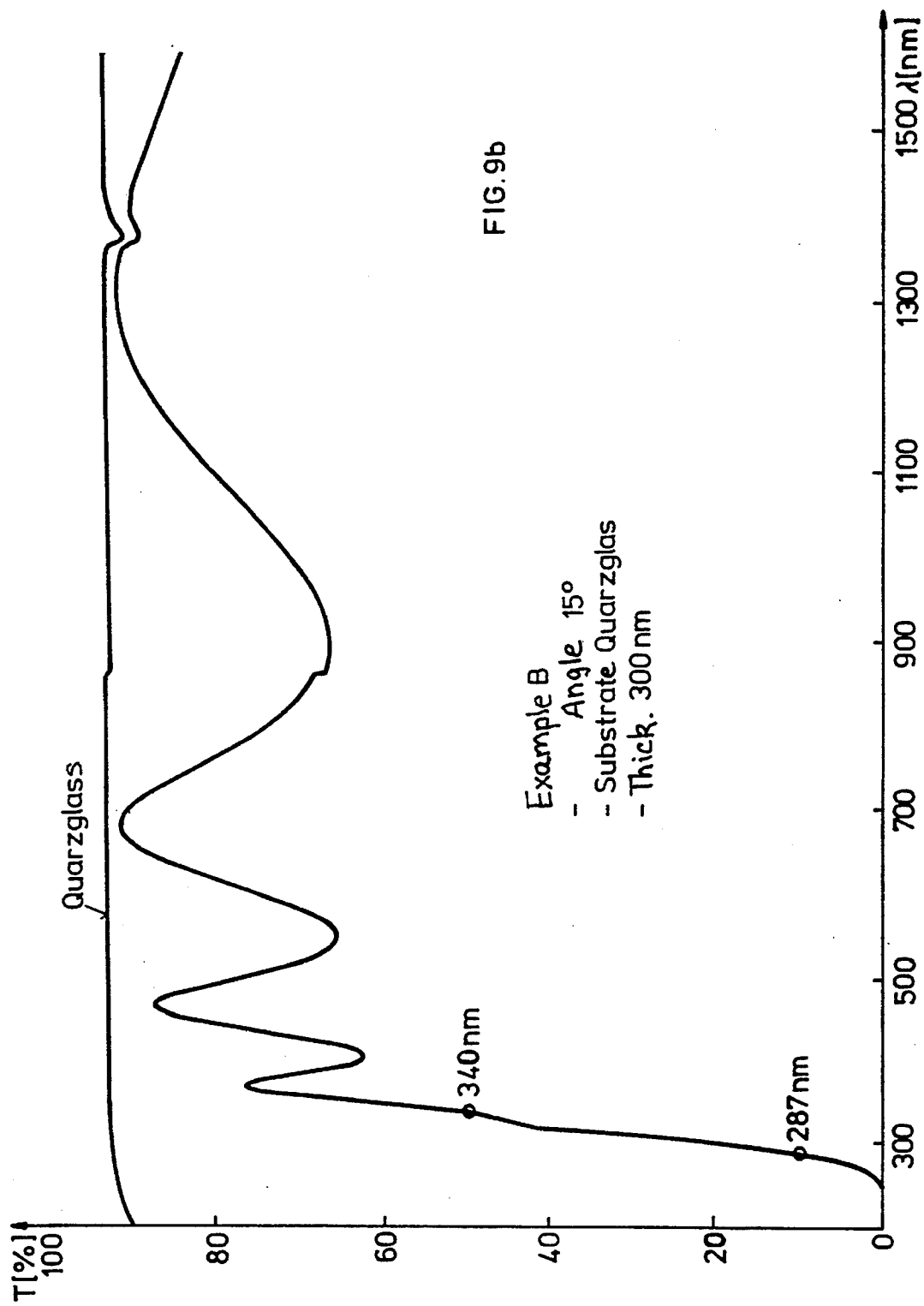

METHOD FOR REALIZING A FILTER EDGE, OPTICAL THIN-FILM AND OPTICAL DEVICE WITH SUCH A FILM

BACKGROUND OF THE INVENTION

1. Field of the Invention

The present invention is generally directed to thin-film optical filters.

More specifically, it is directed to a method for realizing a filter edge of an optical thin-film filter at a desired spectral position, further to an optical thin-film which defines a desired spectral position of a filter edge between a spectral range wherein light is to be blocked and a spectral range wherein light is to be transmitted or reflected. It is further directed to an optical device which comprises an optical filter with at least one optical thin-film and finally to a sun-tanner apparatus which comprises an optical filter device between its ultraviolet source and its optical output where light emits for tanning purposes.

The problems which have been solved by the present invention were specifically recognized in the art of ultraviolet tanning technique. Therefore, such problems are here specifically discussed from the standpoint of that art. Nevertheless, the teaching of the present invention is generally valid on the above-mentioned general art of optical thin-film technology.

2. Description of the Prior Art

In plants for cosmetic purposes and/or therapy, it is known to use ultraviolet high-pressure sources. Such sources in fact emit beside of desired radiation in the UVA spectral range, radiation in the UVC and in the UVB spectral range, as well as in the visible spectral range and in the near infrared spectral range. These spectral ranges are defined as follows:

UVC: 100 nm $\leq \lambda \leq$ 280 nm;
UVB: 280 nm $\leq \lambda \leq$ 315 nm;
UVA: 315 nm $\leq \lambda \leq$ 380 nm;
Visible radiation (VIR): 380 nm $\leq \lambda \leq$ 780 nm;
near infrared radiation (NIR): 780 nm $\leq \lambda \leq$ 1.4 µm.

From the standpoint of human health UVC- and UVB-radiation is not desired and from the standpoint of comfort of persons exposed to that radiation a too strong radiation in the visible and in the near infrared spectral range is also not desired. Therefore, it is customary to perform optical filtering on the radiation emitted from such a source, thereby only transmitting at maximum transmission the desired UVA spectral range radiation.

It is known to use for the realization of such filters so-called ultraviolet glasses, as for instance Uvisol (trademark) M-UG2 of the firm "Deutsche Spezialglas AG". If such ultraviolet glasses (UV-glass) are used, there must be used a clear glass with an according absorption edge so as to accurately block the UVB-radiation which, as known, causes erythema and which, considered in the spectrum, directly follows the UVA-radiation range to be exploited.

The drawbacks of such UV-glasses are that they lead to a certain amount to solarization, i.e. to a shift of the transmission behaviour due to radiation influences and the relatively low transmission within UVA spectral range which is to be exploited. Solarization of the clear glass leads to a shift of its absorption edge toward longer wavelengths so that, during operation, the UVA-radiation part will additionally diminish in an uncontrolled manner. Due to the relatively low UVA-transmission, it is necessary to use UV burners with very high power, so for instance of 2 to 4 kW. This further leads to the necessity that huge efforts and expenditures must be done for appropriate cooling of the apparatus and for generating and applying the high electric power.

Since some time, multilayer interference filters are on the market, for instance produced by applicant of the present invention, which filters consist of alternating thin layers with high and low indices of refraction, so for instance made of $Ta_2O_5$ and of $SiO_2$, respectively. Applied as UVA-band-pass filters, they exhibit a significantly higher UVA-transmission than may be reached with UV-glass filtering technique.

Due to the use of thin metal oxide layers for such optical interference filters, no solarization occurs. A further significant advantage of such interference filters, compared with UV-glass filters is, that the layer material is substantially free of absorption so that a very high UVA-transmission is reached whereby the filtering edges toward the visible spectral range on the one hand and toward the UVB-spectral range on the other hand may be tailored very steep by exploiting interference phenomena. By varying the thickness of the layer, it becomes further possible to shift the filter edges to such spectral positions that the convolution of the transmission curve with the pigmentation curve becomes maximum which leads to optimal tanning and so that the convolution with the erythema curve becomes minimal which leads to the avoidance of sun-burn.

With respect to the definition of the said pigmentation curves and of said erythema curves, attention is drawn on DIN 5031, part 10 and on DIN 5050.

By the use of such interference filters and additional use of coated UVA-reflectors, the required electrical power of some UV-radiation apparatus was significantly reduced, also due to high UVA-transmission.

In the art of such interference filters, there is provided on both sides of a glass substrate a multi thin-layer system. One of them provides for blocking UVB- and UVC-radiation, the other of them blocks visible radiation and radiation in the near infrared spectral range. Primarily based on the both-sided thin-layer coating, the drawback resulting from such systems is that a relatively large number of thin layers, approximately 70, is required which leads to comparatively high manufacturing costs.

In the following description and claims, we understand under the term "thin-film" a film or layer which is produced or deposited on a substrate by a vacuum-coating process, as for instance by a physical vapor deposition process (PVD) or a chemical vapor deposition process (CVD) or a plasma enhanced chemical vapor deposition process (PECVD) or the like. Additionally, such a layer may also be produced by a CVD process at higher than atmospheric pressures.

Considered from the standpoint of general optical filter art, it is known from the FR-A-2 362 412 which accords to the U.S. Pat. No. 4,158,133 and further from the FR-A-2 626 981 a filter technique which makes use of so-called "absorption filters" and of interference filters. The so-called "absorption filters" are in fact described and would also be understood by the man skilled in that art as coloured glass. Thus, these references make use of absorption filters which are not based on thin-film and which do not contribute to the filter action of the thin-film interference filters.

Further attention is drawn to the EP-A-0 410 160 according to the U.S. Pat. No. 5,138,485.

SUMMARY OF THE INVENTION

It is an object of the present invention to remedy the draw-backs of above discussed multi thin-layer interference filters. This is realized in the specific UV-technique by a method for realizing a filter edge in a thin-film optical filter system which comprises at least one thin-film, wherein the filter edge is spectrally located between UVA spectral range wherein light is to be transmitted or to be reflected and UVB spectral range wherein light is to be absorbed which method comprises realizing the filter edge by the material-inherent absorption edge of the material of the thin-film.

Although and as was mentioned above, the object was primarily caused by the need in tanning and therapeutic plants at which predominantly transmission band-pass filters are used, the inventive method may principally be applied for all kinds of optical filters where between the said UV spectral ranges a filter edge must be located for transmitting or reflecting light in the UVA spectral range thereby blocking light in the spectrally neighbouring UVB range.

Compared with known filtering techniques exclusively with interference filters, inventively the filter edge is realized not by exploiting interference phenomena but by exploiting the material inherent absorption edge of the material of a thin-layer which absorption edge being disposed spectrally in-between the spectral range to be transmitted or reflected and the spectral range to be blocked.

For the realization of the said filter edge and according to the proposed method in a minimal configuration, there is provided only one single thin-film of an accordingly selected and composed material.

With respect to the manufacturing of filter and devices which satisfy further needs with respect to spectral filter behaviour, as especially from the standpoint of therapeutical or tanning apparatus for blocking visible radiation and near infrared radiation, the inventively exploited material inherent absorption edge of the material of a thin-film leads to a significant reduction of the required number of interferent thin-films which number remains only given by the additional spectral requirements. Thus the accordingly resulting optical thin-film filter devices, as for instance transmission filters, selective mirrors, may be manufactured at significantly lower prices. As is known, the spectral position of filter edges at optical filters basing exclusively on interference at thin-layers, may be selected by appropriately selecting the thickness of the thin layers.

According to the present invention, it has now been recognized that realizing a filter edge at a predetermined desired spectral position, as especially between UVA-spectral range to be transmitted or to be reflected and UVB-spectral range to be blocked may be realized by exploiting the spectral absorption edge of the thin-film material in that the composition of that thin-film material is appropriately selected. Variation of such composition with respect to the respective materials ratio leads to shifting the spectral position of the material inherent absorption edge, which shifting is exploited to position the absorption edge at a desired spectral position.

It is thus a further object of the present invention to propose a method for realizing a filter edge of an optical thin-film filter at a desired spectral position which comprises the steps of depositing a thin-film of a thin-film material, the composition thereof being of at least two composition materials, a first thereof exhibiting per se a spectral absorption edge above said desired position, a second thereof exhibiting a spectral absorption edge below said desired position and further selecting the ratio of said at least two composition materials of said thin-film material so that the spectral absorption edge of said thin-film material is spectrally located at least approximately at said desired spectral position and exploiting said absorption edge of said thin-film material as said filter edge.

It is a further object of the present invention to provide a method for realizing an optical thin-film band-pass filter which comprises the steps of realizing the filter edge towards shorter wavelengths at least substantially by means of the material inherent absorption edge of a thin-film material and realizing the filter edge towards larger wavelengths by means of thin-film interference.

Thereby thin-film band-pass filters are realized which may be produced at much lower costs than band-pass thin-film filters which exclusively base on interference because the former inventive procedure necessitates a considerably smaller number of interferent thin-films.

In spite of the fact that probably also other materials may be suited as the material of a thin-film, the material-inherent absorption edge of which being inventively exploited as optical filter edge, in a preferred embodiment of the present invention, the material defining the said absorption edge contains at least one of the materials of the following group:

An oxide, an oxinitride, a sulfide, a fluoride respectively of a metal or of a metal-alloy.

Thereby, the spectral position of the desired filter edge which is defined by the material inherent absorption edge of the material of a thin-layer is shifted or adjusted by the selection of at least one of the ratio of the metal or metal-alloy within the said group of material and/or the content of the oxide of said group and/or of an oxinitride of said group and/or the content of a sulfide of said group or of a fluoride of said group or by the ratio of nitrogen to oxygen in an oxinitride of said group.

If we refer to variation of the content of the material inherently defining the absorption edge, we understand all kind of such variation, be it that different crystals are provided in such material and the ratio thereof in that material is varied or be it that in single crystal materials, the structure of such crystals per se is varied, for instance by varying the ratio m/n of a material of the structure $Me_mO_n$ wherein Me is a metal or a metal alloy.

It is a further object of the present invention to propose a material to be selected when the desired filter edge position is between UVB and UVA spectral range which material comprises preferably in a substantial and even in a predominant amount $Nb_2O_5$.

Additionally, it is proposed to add to that $Nb_2O_5$ as further composition material of the thin-film material defining for the absorption edge, $Ta_2O_5$.

Beside of adding $Ta_2O_5$ for accurate shift of the spectral position of the material inherent absorption edge in the thin-film material further comprising preferably to a substantial and even to a predominant portion $Nb_2O_5$, at least one of the following materials may be used:

$HfO_2$, $Al_2O_3$, $SiO_2$, $Y_2O_3$, $ZrO_2$, $ScO_2$, $MgF_2$, $ZnS$ or further fluorides or sulfides.

In further preferred embodiment, the material defining the absorption edge exploited as filter edge comprises at least one of $TaO_xN_y$, $HfO_xN_y$ or $ZrO_xN_y$.

Thereby selection of the spectral position of the inventively exploited absorption edge of the thin-film material is adjusted by appropriate selection of the ratio y/x. Said spectral position may also be selected by appropriate selection of the ratio of oxinitride to a further material in said thin-film material defining for the inventively exploited absorption edge which further material may for instance be an oxide. If the material whose absorption edge is inventively exploited, at least substantially or even predominantly consist of $HfO_xN_y$, the value of $y/(x+y)$ is preferably selected within:

$0.25 \leq y/(x+y) \leq 0.5$, thereby preferably to $0.25 \leq y/(x+y) \leq 0.45$ and even in a preferred mode to be approx. 0.35, thereby selecting the desired spectral position between UVA- and UVB-spectral range.

Following the further object of the present invention, namely to provide for utmost flexibility in the selection of appropriate thin-film material defining for the inventively exploited material inherent absorption edge, it is further proposed to provide in this material predominantly $Zr_xN_y$ or $TaO_xN_y$, thereby selecting the desired spectral position of the filter edge realized by material inherent absorption edge between UVA- and UVB-spectral ranges.

Further, under this object it is proposed to provide in this material predominantly at least one of $TiO_2$ and of ZnS.

Beside of the object to propose the above mentioned inventive method, it is a further object of the present invention to propose an optical thin-film for defining the desired spectral position of a filter edge. This is resolved in that the optical thin-film for defining a desired spectral position of a filter edge between a spectral area wherein light is to be transmitted and a spectral area wherein light is to be blocked is made of a material which comprises at least two composition materials, the spectral position of the material inherent absorption edge of the thin-film material being defined by the ratio of the at least two composition materials and being at least approx. at the spectral position which is desired for the filter edge.

The object of the invention, namely of appropriately shifting the material inherent absorption edge spectrally to a desired position is resolved at the inventive optical thin-film in that its material has one composition material defining per se an absorption edge below the desired spectral position of the filter edge and a second composition material which defines per se an absorption edge spectrally above the desired spectral position of the filter edge. Thus, by appropriate selection of the ratio of the two composition materials, the resulting absorption edge of the composition thin-film material is selected.

Further object of the inventive optical thin-film and its specific preferred features to resolve such object will become evident to the man skilled in the art when considering the further description and the claims. Beside of proposing the inventive method of filter realization and of the inventive optical thin-film, it is a further object of the present invention to provide for an optical device which comprises an optical filter with at least one thin film which fulfills several purposes with respect to tailoring the spectral chracteristics of such device. This object is resolved by such an optical device wherein a filter edge is defined by the absorption edge of the material of the thin-film, namely by the material composition of the thin-film material.

It is a further object of the present invention to provide an optical thin-film band-pass filter device which makes use of thin-film interference but with a significantly reduced number of thin-films compared with prior art filters whereat both filter edges are realized by thin-film interference. This latter object is resolved by an optical device which comprises an optical thin-film band-pass filter and whereat the filter edge towards shorter wavelengths is at least substantially defined by the absorption edge material-inherent to the material of at least one thin-film and whereat the filter edge towards longer wavelengths is substantially defined by interference at thin-films. Thereby only the upper filter edge governs the number of thin-films to be provided.

Further objects and preferred features of the inventive optical device will become apparent to the man skilled in the art when reading the following description and claims.

It is a further object of the present invention to provide a sun-tanner apparatus at which for a given cosmetic or therapeutic effect considerably less electric energy must be installed, which further is less expensive in manufacturing and nevertheless leads—with respect to health and comfort—even to considerable advantages.

This is resolved by the sun-tanner apparatus which comprises an optical filter device between its ultraviolet source and its optical output for tanning and whereat the optical filter device comprises an optical band-pass filter transmitting light in the UVA range and blocking light in the UVB range and in the visible and/or near infrared spectral range and whereat the filter edge between UVB and UVA spectral range is realized by the material inherent absorption edge of the material of a thin-film of an interference filter, the filter edge towards larger wavelengths being realized by the interference filter itself.

Other objects, advantages and preferred features of the inventive sun-tanner apparatus will become evident to the man skilled in the art when reading the description and claims of the present application.

BRIEF DESCRIPTION OF THE DRAWINGS

The present invention under all its aspects will be better understood and objects other than those set forth above, will become apparent to the man skilled in the art when consideration is given to the following detailed description thereof. Such description makes reference to the annexed drawings wherein:

FIGS. 9a, 9b and 9c show three spectral transmission characteristics of $HfO_xN_y$-thin-films for different y/x ratios.

DESCRIPTION OF THE PREFERRED EMBODIMENT

Figure 1:
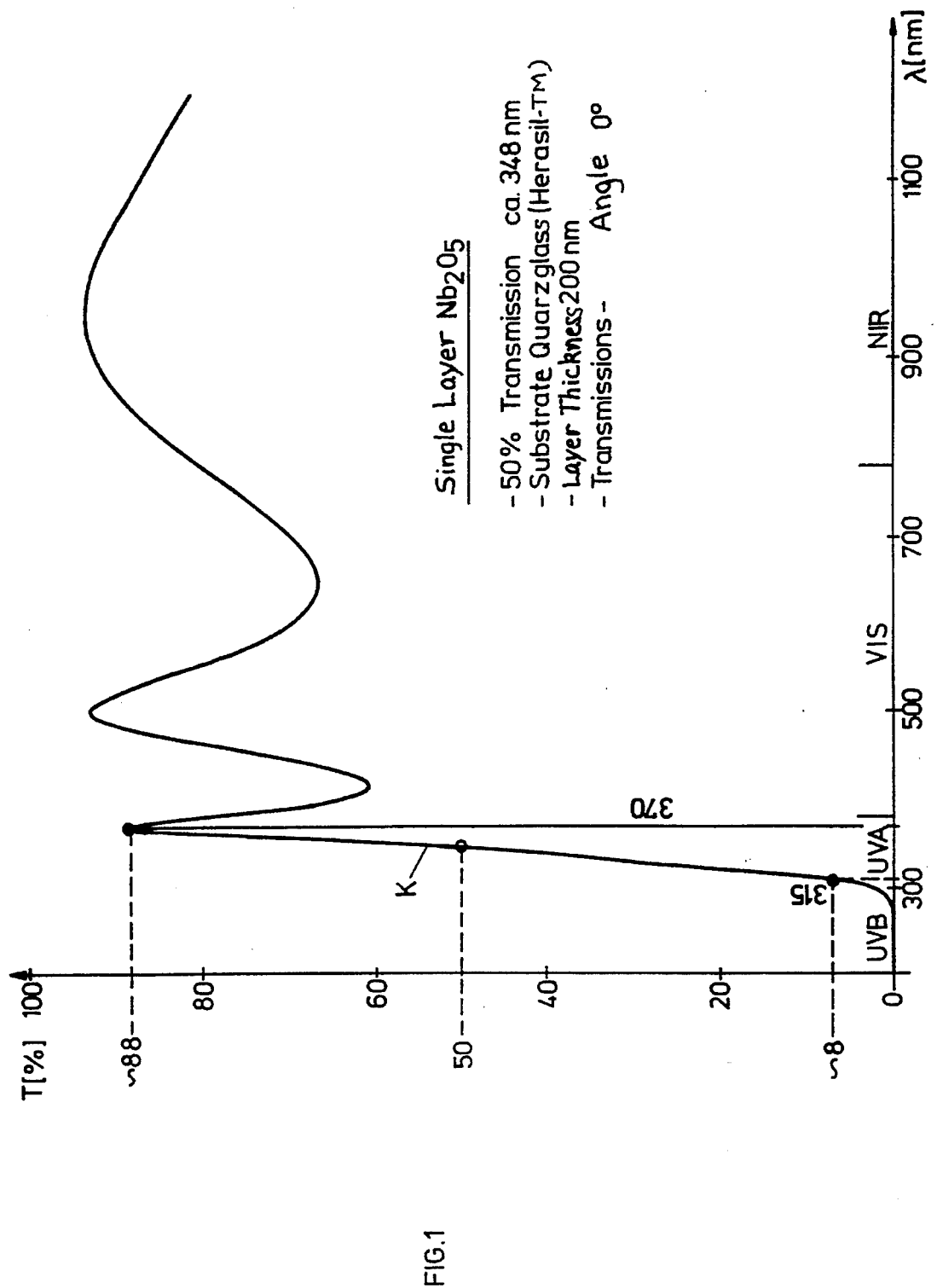
FIG. 1 shows the characteristic of spectral transmission of an inventive thin-film material which, has in the preferred mode, a material inherent absorption edge between UVB- and UVA-spectral range and is, as a further preferred embodiment, realized by $Nb_2O_5$ thin-film material applied to quartz glass, e.g. to HERASIL (trademark)

In FIG. 1 there is shown the spectral transmission characteristic of an inventively preferred thin-film material, namely of $Nb_2O_5$. The transmission characteristic was measured at a $Nb_2O_5$-single-layer with a thickness d=200 nm and applied on a substrate of quartz glass. For clearness sake, the spectral ranges defined above are shown on the wavelength axis of FIG. 1.

Therefrom it becomes evident that the material inherent absorption edge K of $Nb_2O_5$ passes the 50% value at a wave-length of light of approx. 348 nm. This means that for light of 348 nm the absorption and the remaining reflection is approx. 50%. For $Nb_2O_5$ there is proposed a minimum thickness of film of 10 nm, preferably a thickness of minimum 200 nm.

If such material is used as a material of two or more thin-films in a multifilm or multilayer system, the latter indications with respect to thickness are valid for the sum of all thicknesses of such thin layers of that material provided at this system.

Figure 2:
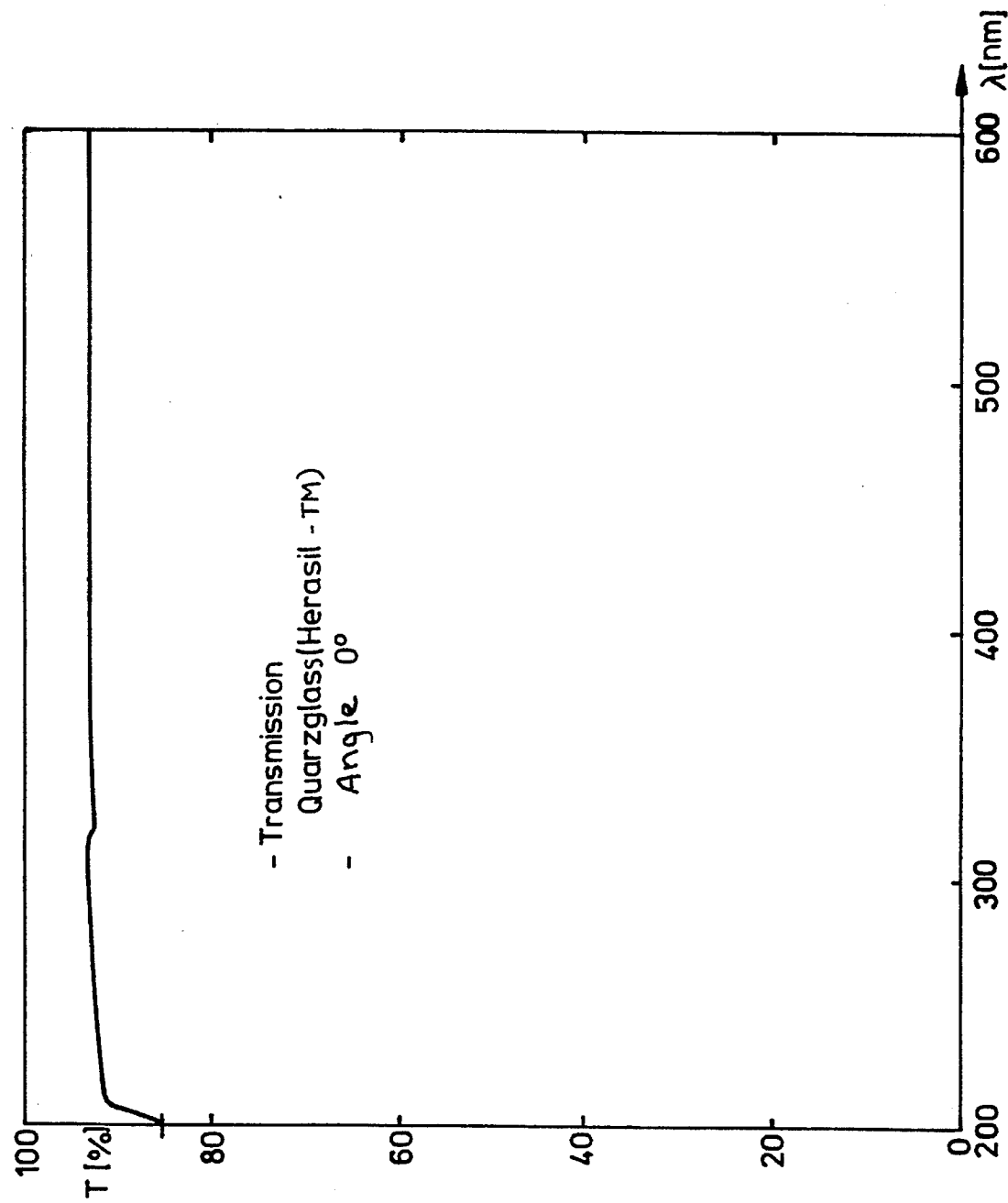
FIG. 2 shows the spectral transmission characteristic of quartz glass, namely of HERASIL (trademark)

It becomes further evident that there is realized a good blocking of the UVB spectral range at high transmission in the UVA spectral range due to the material inherent absorption characteristic of $Nb_2O_5$. With a limit spectral value between UVA and UVB spectral ranges, as defind above, namely of 350 nm, there remains a transmission of less than 8% according to an absorption and remaining reflection of more than 92% in UVB whereas at the wavelength of 370 nm, the transmission is approx. 88% according to a remaining absorption and reflection of approx. 12%, in the UVA range. In FIG. 2 there is shown the spectral transmission characteristic of the substrate material used, namely of quartz glass (HERASIL, trademark).

Figure 3:
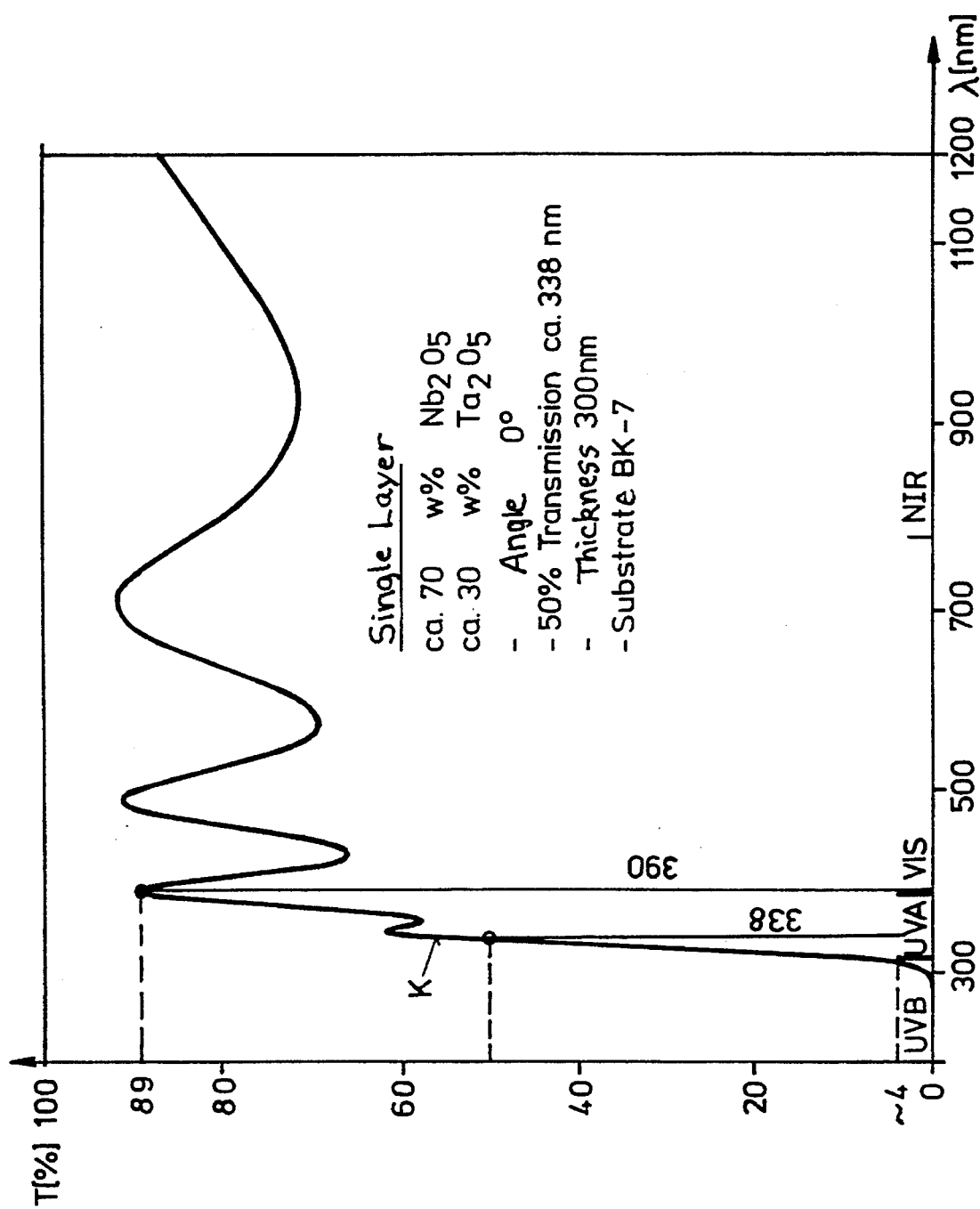
FIG. 3 shows, in a representation according to FIG. 1, the spectral transmission characteristic of a further preferred and inventively exploited thin-film material, namely of a material consisting of approx. 70% by weight of $Nb_2O_5$ and of approx. 30% by weight $Ta_2O_5$, the material being applied on BK-7-Glass.

In FIG. 3 the transmission characteristic is shown in an analogue manner to FIG. 1. The transmission characteristic of that figure results from a further preferred thin-film material for separating UVB and UVA spectral ranges which material consists of approx. 70% by weight $Nb_2O_5$ and approx. 30% by weight $Ta_2O_5$. As for the characteristic of FIG. 1 the characteristic of FIG. 2 is measured with the perpendicular impingement of light at a single film with a thickness of 300 nm applied on BK-7 glass. It becomes evident that at the limit wavelength of 315 nm the absorption and remaining reflection is approx. 96% and that the minimum absorption and remaining reflection according to maximal transmission of approx. 89% occurs at a wavelength of approx. 390 nm. The 50% transmission and thus absorption and remaining reflection point is approx. at 338 nm. With this composite material, it is proposed a minimum layer thickness of 10 nm; preferably, there is proposed a minimum layer thickness of 250 nm. If this inventive material is applied as the material of two or more thin-films in a multifilm or multilayer system, the said indications with respect to thickness are valid for the sum of the thicknesses of all such films provided of said material.

Figure 4:
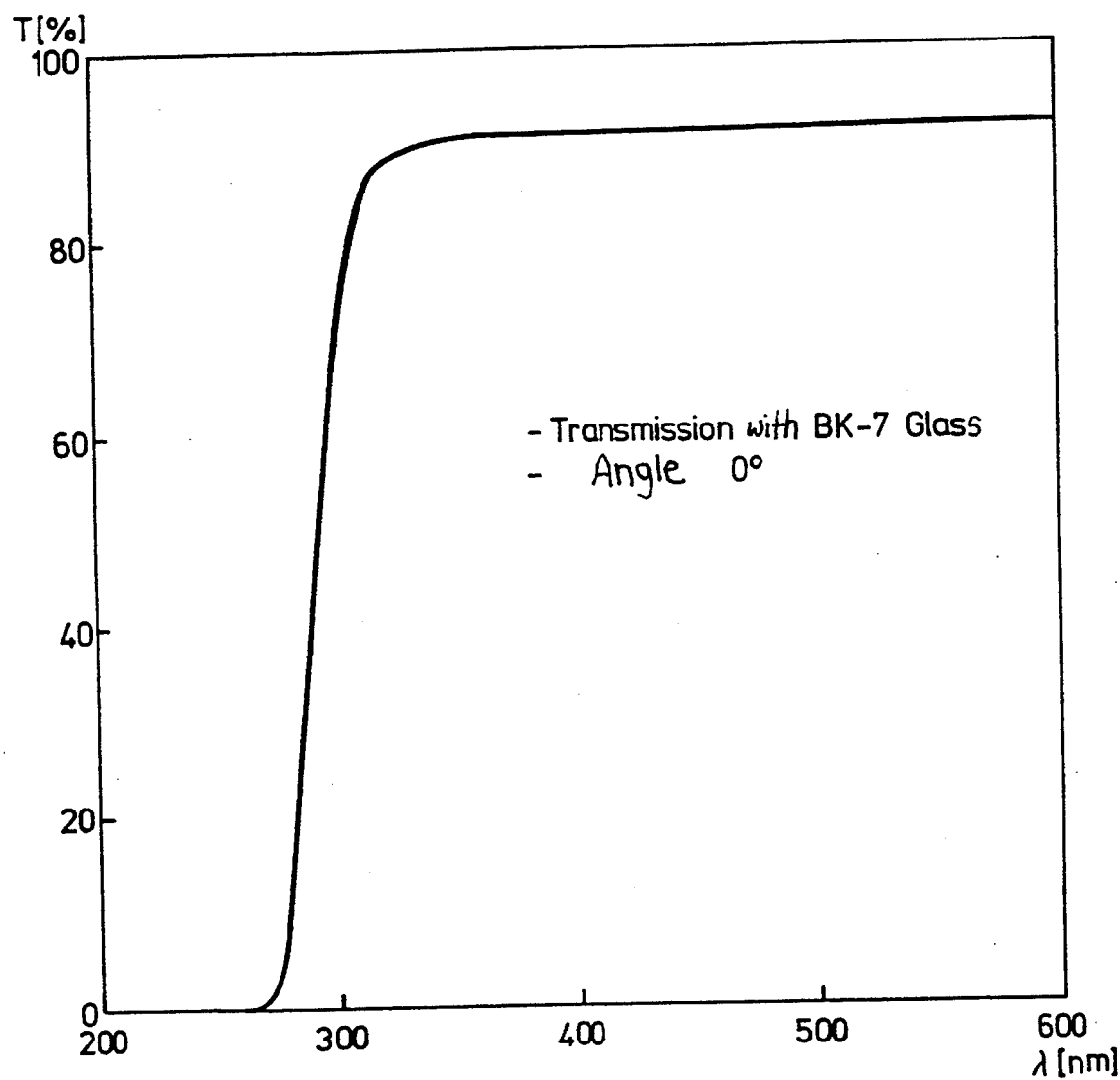
FIG. 4 shows the spectral transmission of BK-7 glass.

FIG. 4 shows the spectral transmission characteristic of BK-7 glass.

Figure 7:
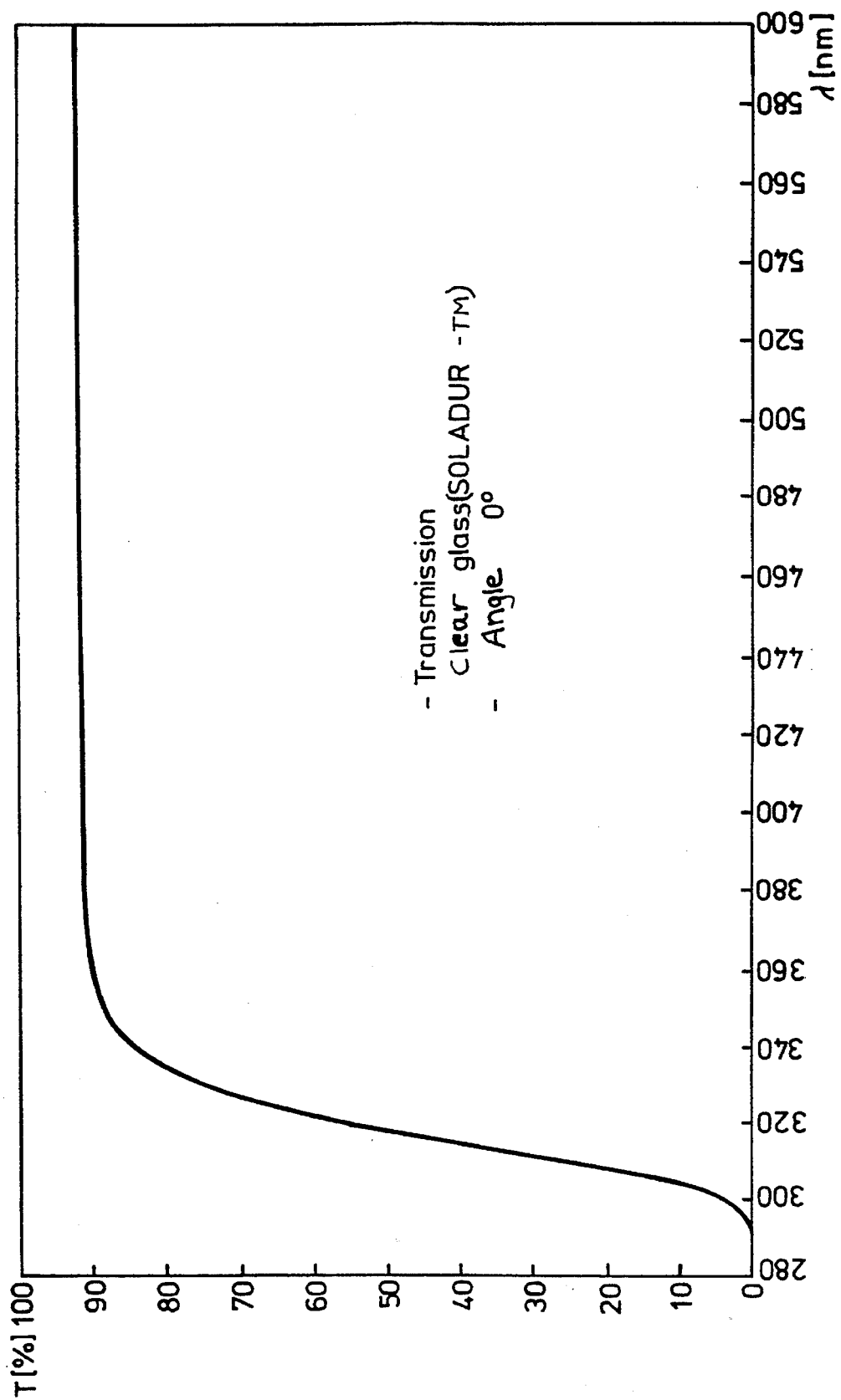
FIG. 7 shows the spectral transmission characteristic of clear glass, namely of SOLADUR (trademark)

With the inventive and preferred material consisting of approx. 70% by weight of $Nb_2O_5$ and approx. 30% by weight of $Ta_2O_5$, there was construed a transmission filter on a clear glass substrate of SOLADUR from the firm Desag. The resulting transmission characteristic of that glass is shown in FIG. 7. The transmission filter was especially tailored for the needs of UV cosmetic or therapeutic tanner plants. This means that beside of blocking UVB- and UVC-radiation, blocking of radiation in the visual and in the near infrared spectrum was a target. The SOLADUR glass substrate was only coated on one side and the thin-film, the absorption edge of the material of which was inventively exploited to define for the filter edge between UVB and UVA spectral range was also used as thin-film of an interference thin-film filter. In other words, that thin-film did on the one hand define the lower wavelength filter edge and did on the other hand co-define the upper filter edge by interference with other thin-films. Thereby this thin-film was with respect to interference a thin-film of higher refractive index and was combined with thin-films of lower refractive index made of $SiO_2$. The filter is construed departing from the glass substrate as follows:

| | Substrate: SOLADUR (FIG. 7) | |
| --- | --- | --- |
| | Structure: | |
| Material of Substrate | Thickness | Repetition Factor |
| A | 64,5 nm | 1x |
| B | 90 nm | |
| A | 53,8 nm | 4x |
| B | 85 nm | |
| A | 58 nm | 1x |
| B | 95 nm | |
| A | 64 nm | 5x |
| B | 108 nm | |
| A | 71 nm | 1x |
| B | 135 nm | |
| A | 85 nm | 4x |
| B | 138 nm | |
| A | 68 nm | 1x |
| B | 53 nm | |
| | Air | |

A: inventive material (70% by weight $Nb_2O_5$, 30% by weight $Ta_2O_5$
B: $SiO_2$ This filter with its interferent thin-films was produced by electron beam evaporation, on the one hand of the composite material ($Nb_2O_5$, $Ta_2O_5$) and, on the other hand, of $SiO_2$.

As was mentioned above, it shall be repeated that techniques for depositing thin-film layers also of the inventive material are widely known to the man skilled in the art and are not critical with respect to their selection. Thus, such thin-films may be deposited by:
Evaporation:
  by electric heating from a crucible;
  by electron beam evaporation; preferably ion-enhanced;
Sputtering: with AC, DC or AC+DC, by ion-beam;
Ion plating, etc.
or by any CVD- or PECVD-methods or hybrid techniques.

The layers may thereby be deposited by reactive vacuum deposition methods or, as was done for the above mentioned filter by non-reactive.

Composite materials may further be deposited by provision of separate composition material sources or may be, as was done for realizing the above-mentioned filter, applied from a unitary one composite material source.

Figure 5:
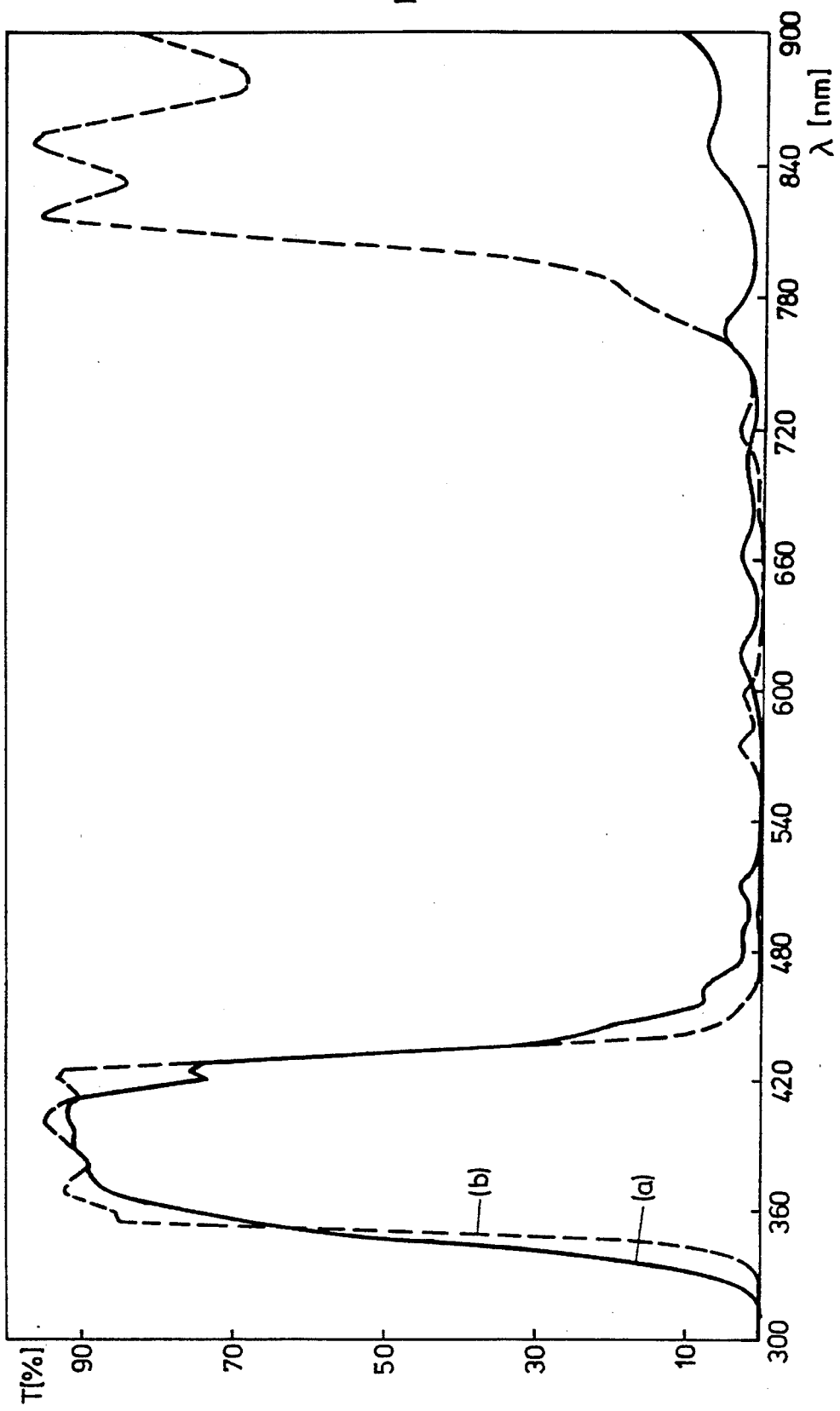
FIG. 5 shows the spectral transmission characteristic of an inventive optical device tailored as transmission filter device, especially tailored for the needs in sun-tanning technique at curve (a) and shows the spectral transmission characteristic of a prior art interference filter produced and sold by applicant of the present application at curve (b)

In FIG. 5 the continuously drawn characteristic (a) shows the transmission characteristic of the above-mentioned filter. Whereas the band-pass filter edge between UVA spectral range and UVB spectral range is substantially given by the material inherent absorption edge of the $Nb_2O_5$—$Ta_2O_5$ composite material according to FIG. 3, the filter edge which separates the UVA-spectral range with respect to the visual spectral range is given by interference at the thin-film structure as defined in the above table.

At such an optical band-pass filter element, thus and inventively, the filter edge towards smaller wavelengths is substantially defined by the absorption edge of the material of a thin-film, here of the specified composite material, whereas the filter edge towards higher wavelengths is realized by interference. There is exploited inventively one or more than one thin layers made of selected material with its material inherent absorption edge simultaneously as thin-film of the interference filter system thereby preferably as higher refractive index thin-films of said interference filter system.

Nevertheless, it is absolutely and inventively possible to apply for an interference filter system, thin layers of two materials which do not fulfill the inventively exploited requirements with respect to absorption edge. Then there is applied at least one additional thin film which latter is then made of a material which does fulfill the inventively exploited requirements with respect to absorption edge and the thickness of which is tailored to accurately block light in the spectral range to be blocked.

In FIG. 5 there is shown in dotted lines (b) the transmission characteristic of a known UV filter which is construed of two multiple thin-film systems on either side of the substrate, i.e. of a system as was discussed in the introductory part. This prior art comparison filter according to (b) has the following structure:

Prior Art (Thicknesses in nm)

| Substrate one side | | Substrate the other side | |
|---|---|---|---|
| Thickness | Rep. Factor | Thickness | Rep. Factor |
| A 18 | | A 70 | |
| B 45 | | B 83 | |
| A 36 | 1 | A 62 | 1 |
| B 43 | | B 83 | |
| A 35 | 7 | A 57 | 6 |
| B 50 | | B 83 | |
| A 34 | | A 65 | |
| B 43 | 1 | B 72 | 1 |
| A 34 | | | |
| B 98 | | | |
| | | A 69 | 6 |
| Air | | B 99 | |
| | | A 77 | 1 |
| | | B 119 | |
| | | A 82 | 6 |
| | | B 119 | |
| | | A 66 | 1 |
| | | B 52 | |
| | | Air | |

A: $Ta_2O_5$
B: $SiO_2$

Figure 6:
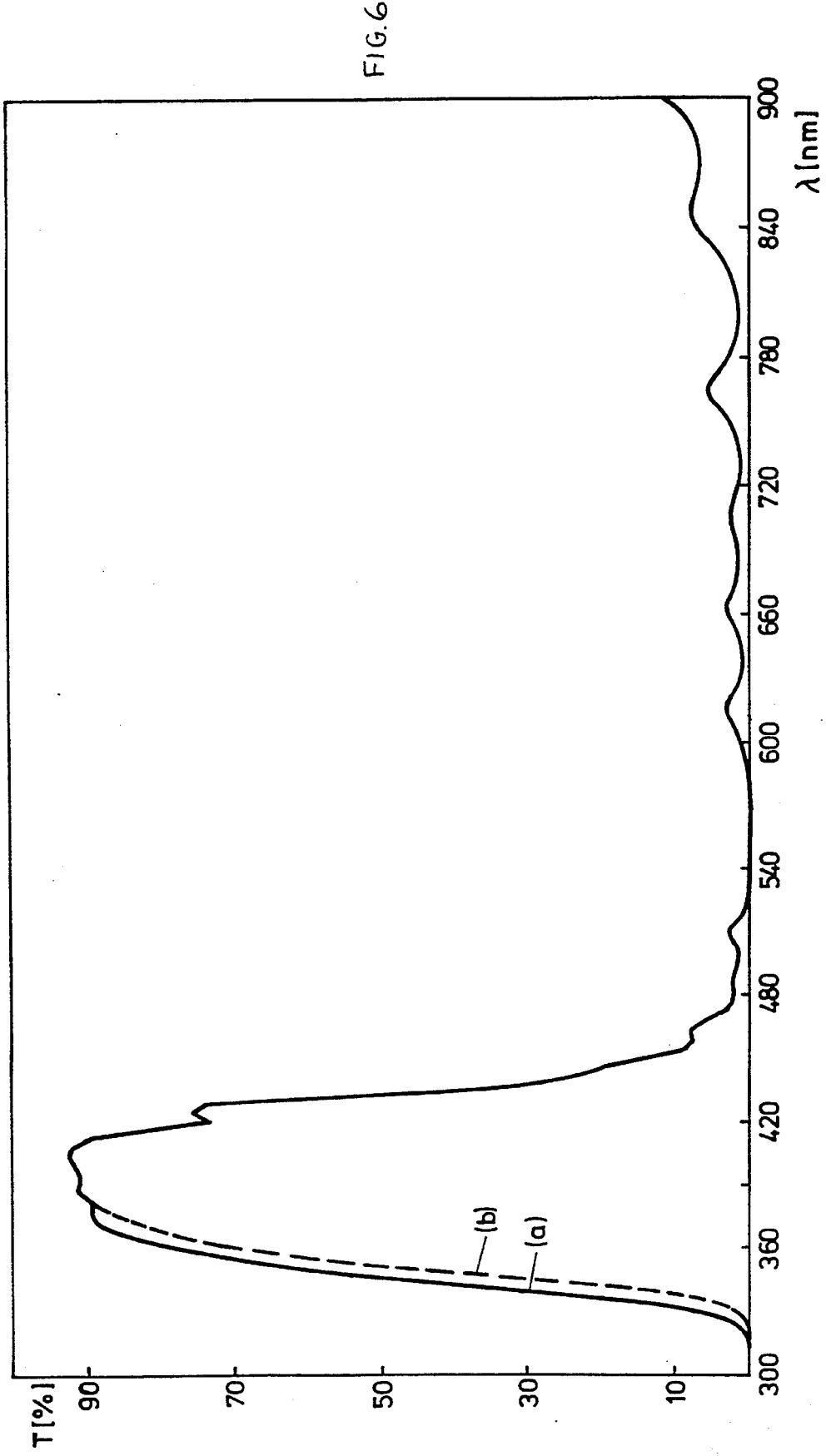
FIG. 6 shows the spectral transmission characteristic of the inventive optical transmission filter according to FIG. 5 curve (a) and, in dotted line, the characteristic for a shifted spectral position of the absorption edge, as shifted by varying the composition of the thin-film material.

In FIG. 6 there is shown drawn in continuous line the transmission characteristic (a) according to FIG. 5 at (a) of the inventive filter.

In dotted lines FIG. 6 shows the spectral transmission characteristic if, departing from the filter defined above, there is used a composite material of approx. 60% by weight $Nb_2O_5$ and approx. 40% by weight $Ta_2O_5$. Clearly evident is the shift of the resulting filter edge, defined by the material inherent absorption edge between UVA and UVB spectral ranges which, with respect to filter (a) according to FIG. 5, is shifted in direction to bigger wavelengths (b).

By specifically optimizing the composition of the thin-film whose absorption edge is inventively exploited, there may be achieved maximizing of UVA transmission and thereby minimizing of UVB transmission. If at both filters according to FIG. 5, namely at the prior art filter according to (b) and the inventive filter according to (a), the transmitted optical power is measured in the UVB range, in the UVA range and in the near infrared range and the transmitted power in the UVA range is weighted with the pigmentation curve according to DIN 5031, part 10, there results that with the inventive filter the pigmentation achieved is somewhat better than with the known comparison filter according to (b) of FIG. 5. Further, the transmitted power in the UVB range is approx. 25% smaller for the inventive filter than for the prior art comparison filter and the transmitted power in the near infrared range is approx. 20% lower at the inventive filter than at the prior art comparison filter.

Thus, it becomes inventively possible to construe optical filters and especially UV filters for tanning apparatus or plant at reduced costs which filters meet filtering requirements at least as well as prior art interference UV filters with multifilm systems applied to both sides of a substrate.

As was mentioned, FIG. 7 shows the spectral transmission characteristic of clear glass, namely of SOLADUR.

Further, thin-layers of $HfO_xN_y$ and $ZrO_xN_y$ were investigated. For instance, the following table shows data of the investigated $HfO_xN_y$-data.

$HfO_xN_y$ - THIN-LAYERS APPLIED ON QUARTZ-GLASS

| Nr | 10%-Tr at | 50%-Tr at | y/(x + y) ($N_2$-Content) | Thickness |
|---|---|---|---|---|
| A | 262 nm | 300 nm | ca 25/100 | 400 nm |
| B | 287 nm | 340 nm | ca 35/100 | 300 nm |
| C | 356 nm | 400 nm | ca 45/100 | 300 nm |

Figure 8:
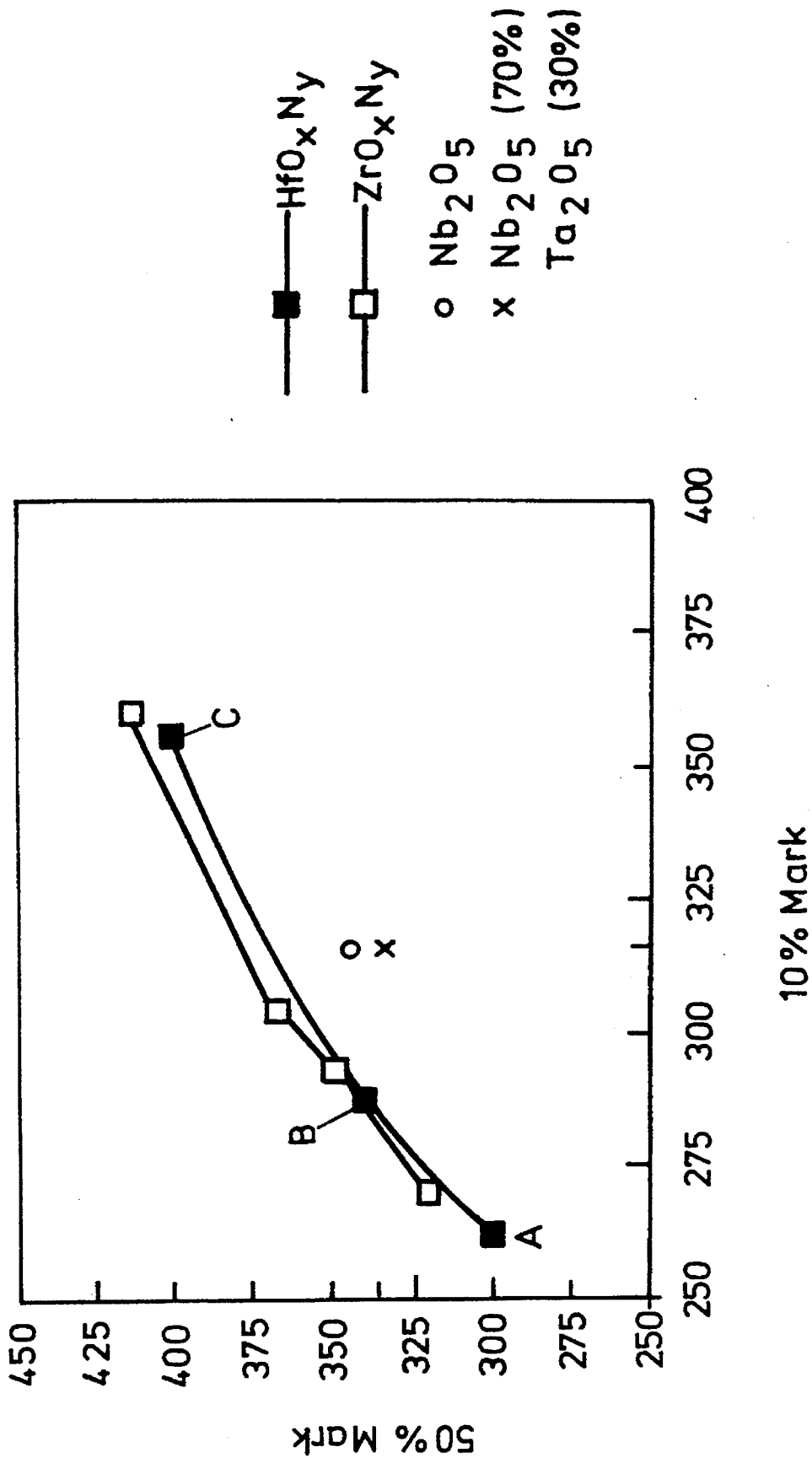
FIG. 8 shows the distribution of the 50% transmission points and of the 10% transmission points for $HfO_xN_y$ and for $ZrO_xN_y$ for varying y/x ratios and of $Nb_2O_5$ and of $Nb_2O_5$ at 70% by weight and $Ta_2O_5$ at 30% by weight.
Figure 9C:
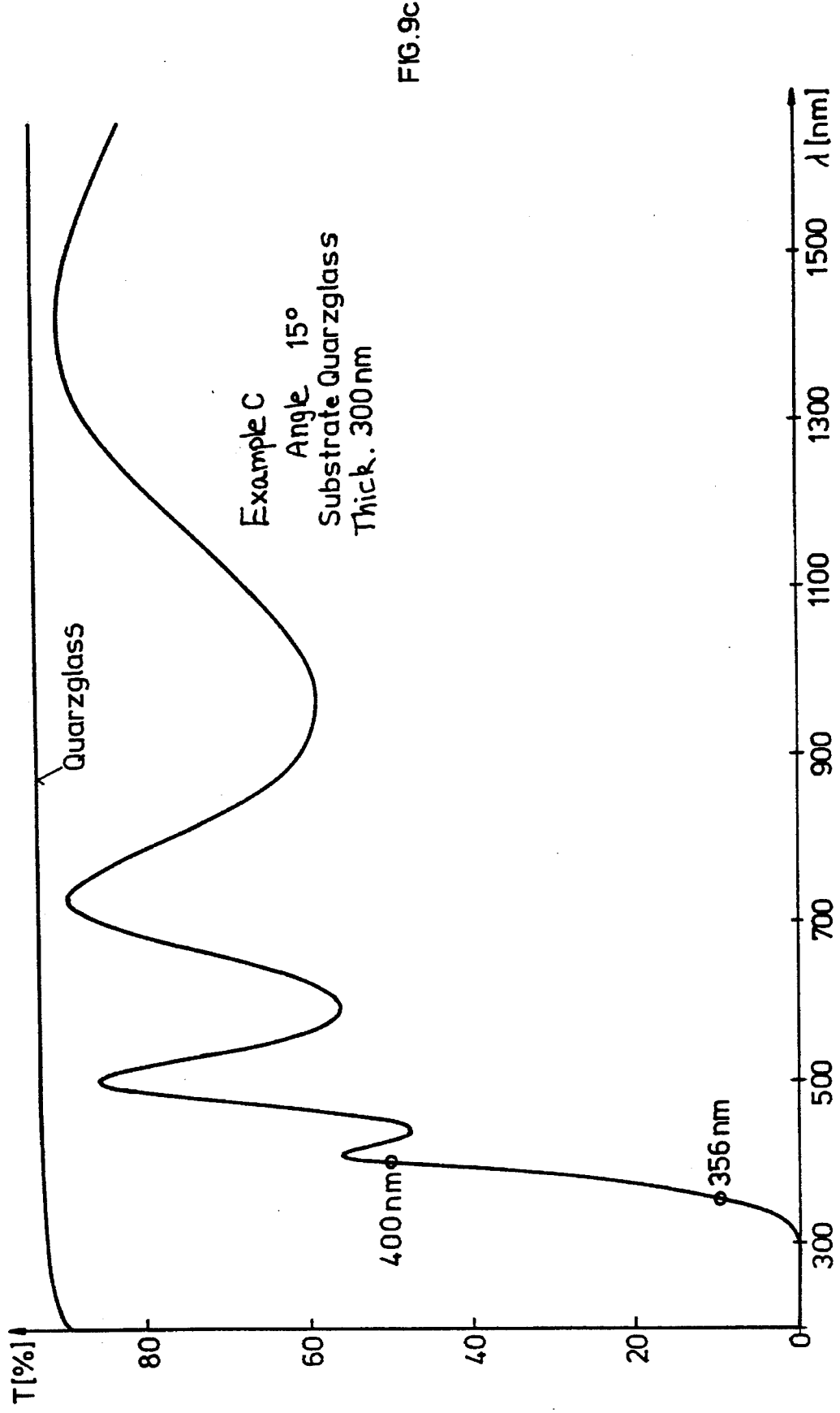

The resulting 10% and 50% transmission values of the said $HfO_xN_y$ thin-films are shown in FIG. 8. Additionally, in that figure the 10%/50% transmission values which resulted for $ZrO_xN_y$ at varying nitrogen content in the thin-layer material are shown and additionally, for comparison, the values $Nb_2O_5$ according to FIG. 1 and of the composite $Nb_2O_5/Ta_2O_5$ thin-film material according to FIG. 3.

Therefrom it becomes evident that, especially for separation of UVB-spectral range and UVA-spectral range, oxinitrides may be used whereat the spectral position of the absorption edge is controlled by the ratio y/x in an accurate manner. It is clear that for other filter requirements in other spectral ranges other material may be used, especially oxides, sulfides, fluorides and oxinitrides of metals or of metal alloys or of composite material with at least one of these materials.

FIG. 8 shows clearly how inventively the spectral position of the material inherent absorption edge may be selected and shifted by varying the composition of the thin-layer material, here of the nitrogen to oxigen partition.

We claim:

1. A method for realizing a filter edge of an optical absorption filter with at least one thin film at a desired spectral position, comprising the steps of depositing a thin film material, comprising at least two composition materials, a first thereof exhibiting per se a spectral absorption edge above said desired spectral position, a second thereof exhibiting a spectral absorption edge below said desired spectral position;

selecting the ratio of said two composition materials within said thin film material so that the resulting spectral absorption edge of said thin film material is spectrally located at least approximatively at said desired spectral position;

exploiting said resulting absorption edge of said thin film material as said filter edge.

2. The method of claim 1, further comprising the step of exploiting said resulting absorption edge of said thin film material as the lower filter edge of an optical thin film band-pass filter and realizing the upper edge of said optical thin-film band-pass filter by means of interference at thin films.

3. The method of claim 1 further comprising the step of selecting said desired spectral position between UVA spectral range and UVB spectral range.

4. The method of claim 1 further comprising the step of selecting at least one of an oxide, an oxinitride, a sulfide or a fluoride respectively of a metal or of a metal alloy as at least one of said composition materials.

5. The method of claim 4 further comprising the step of adjusting said spectral position of said resulting absorption edge of said thin film material by adjusting at least one of:
  the ratio of metal of said metal alloy;
  the content of said oxide in said film material;
  the content of said oxinitride in said film material;
  the content of said sulfide in said film material;
  the content of said fluoride in said film material;
  the ratio of nitrogen to oxygen in said oxinitride in said film material.

6. The method of claim 1 comprising the step of selecting $Nb_2O_5$ as at least one of said composition materials and selecting said desired spectral position between UVB and UVA spectral range.

7. The method of claim 6 comprising the step of providing as a further composition material $Ta_2O_5$.

8. The method of claim 7 comprising the step of providing $Ta_2O_5$ as a substantial part of non-$Nb_2O_5$-material of said thin film material.

9. The method of claim 6 further comprising the step of providing at least 50% by weight of $Nb_2O_5$ in said thin film material.

10. The method of claim 6 further comprising the step of providing at least 60% by weight of $Nb_2O_5$ in said thin film material.

11. The method of claim 6 further comprising the step of providing at least 70% by weight of $Nb_2O_5$ in said thin filter material.

12. The method of claim 1 further comprising the step of providing said resulting absorption edge of said thin film material at a spectral position between UVA and UVB spectral range by providing approx. 70% per weight of $Nb_2O_5$ and approx. 30% by weight of $Ta_2O_5$ in said thin film material.

13. The method of claim 1 further comprising the step of providing in said thin film material at least one of $TaO_xN_y$, $HfO_xN_y$, $ZrO_xN_y$.

14. The method of claim 13 further comprising the step of selecting spectral position of said resulting absorption edge of said thin film material by selection of the ratio y/x of said x and y.

15. The method of claim 13 further comprising the step of selecting spectral position of said resulting absorption edge of said thin film material by selection of the ratio of said thin film material by selection of the ratio of said at least one of said oxinitrides to further material of said at least one thin film material.

16. The method of claim 13 further comprising the step of providing in said thin film material $HfO_xN_y$, and selecting y/(x+y) as follows:

$$0.25 \leq y/(x+y) \leq 0.5.$$

17. The method of claim 16 thereby selecting y/(x+y) as follows:

$$0.25 \leq y/(x+y) \leq 0.45.$$

18. The method of claim 17 thereby selecting y/(x+y) to be approx. 0.35, and selecting said desired spectral position between UVA and UVB spectral range.

19. The method of claim 13 thereby providing in said film material is substantially $ZrO_xN_y$ and selecting said desired spectral position between UVA- and UVB-spectral range.

20. The method of claim 13 comprising the step of providing in said film material is substantially $TaO_xN_y$ and selecting said desired spectral position between UVA- and UVB-spectral range.

21. The method of claim 1 thereby providing in said thin film material at least one of $TiO_2$ and of ZnS.

22. A method for realizing a filter edge in a thin film optical absorption filter system comprising at least one thin film, said filter edge being spectrally located between UVA spectral range, wherein light is to be transmitted or to be reflected, and UVB spectral range, wherein light is to be absorbed, comprising the step of exploiting the material inherent absorption edge of the material of said thin film as said film edge.

23. A method for realizing an optical thin film band-pass filter comprising the step of exploiting the material inherent absorption edge of a thin-film material as filter edge towards shorter wavelengths and realizing the filter edge towards larger wavelengths by means of thin-film interference.

24. The method of claim 23, further comprising the step of selecting spectral position of said material inherent absorption edge between UVA- and UVB-spectral range by selecting the composition of said thin-film material.

25. An optical thin film for defining a desired spectral position of a filter edge between a spectral area wherein light is to be transmitted and a spectral area wherein light is to be blocked absorption, the material of said thin film comprising at least two composition materials, the spectral position of the material inherent absorption edge of said thin film material being defined by the ratio of said at least two composition materials and being at least approximately at the spectral position of said filter edge.

26. The optical thin-film of claim 25, wherein said thin-film material has one composition material defining per se an absorption edge below said desired spectral position of said filter edge and a second composition material defining per se an absorption edge above said desired spectral position of said filter edge.

27. The optical thin-film layer of claim 25, wherein said desired spectral position is between UVB-spectral range and UVA spectral range and wherein said optical thin-film transmits light in the UVA spectral range and absorbs light in the UVB spectral range.

28. The optical thin-film layer of claim 25, said thin-film material comprising at least $Nb_2O_5$.

29. The optical thin-film layer of claim 28, wherein said desired spectral position is between UVB- and UVA-spectral range.

30. The optical thin-film of claim 28, wherein said thin-film material further comprises $Ta_2O_5$.

31. The optical thin-film of claim 25, wherein said thin-film material comprises at least 50% by weight of $Nb_2O_5$.

32. The optical thin-film layer of claim 25, wherein said thin-film material comprises at least 60% by weight of $Nb_2O_5$.

33. The optical thin-film layer of claim 25, wherein said optical thin-film material comprises at least 70% by weight of $Nb_2O_5$.

34. The optical thin-film layer of claim 25, wherein said optical thin-film material comprises at least 50% by weight of $Nb_2O_5$ and wherein the remainder of said thin-film material comprises at least 50% by weight $Ta_2O_5$.

35. The optical thin-film of claim 25, the material of said thin-film comprising at least one of an oxide, an oxinitride, a sulfide and a fluoride, respectively of a metal or of a metal alloy.

36. The optical thin-film layer of claim 35, wherein the spectral position of said absorption edge of said thin-film material is defined by at least one of:

the ratio of metals in said metal alloy;

the content of said oxide;

the content of said oxinitride;

the content of said sulfide;

the content of said fluoride;

the ratio of nitrogen to oxigen of said oxinitride.

37. The optical thin-film layer of claim 25, the material thereof consisting of at least 50% by weight $HfO_xN_y$ and wherein there is valid:

$0.2 \leq y/(x+y) \leq 0.5$.

38. The optical thin-film layer of claim 37, wherein there is valid:

$0.25 \leq y/(x+y) \leq 0.45$.

39. The optical thin-film layer of claim 38, wherein:

$y/(x+y)$ is approx. 0.35.

40. The optical thin-film layer of claim 25, the material thereof consisting substantially of at least one of $ZrO_xN_y$, $TaO_xN_y$, $TiO_2$ and ZnS.

41. An optical absorption device comprising an optical filter with at least one optical thin-film, wherein a filter edge is defined by the absorption edge of the material of said thin-film which absorption edge being defined by the material composition of said thin-film material.

42. The optical device of claim 41, comprising an optical thin-film band-pass filter, the filter edge towards shorter wavelengths being substantially defined by said absorption edge, the filter edge towards longer wavelengths being substantially defined by interference at thin-films.

43. The optical device according to claim 41, comprising an interference thin-film filter, wherein said optical thin-film defining said absorption edge is simultaneously a thin-film defining for the spectral characteristics of said interference filter.

44. The optical device of claim 43, wherein a filter edge defined by interference is locally at a different spectral range than said filter edge defined by said absorption edge.

45. The optical device of claim 41, wherein said filter is a transmission band-pass filter transmitting light in the UVA spectral range and with said absorption edge defining for a filter edge towards UVB spectral range and further comprising thin-film interferent layers defining for a filter edge towards larger wavelengths of said band-pass filter which filter blocking light in the visible and/or in the near infrared spectral range.

46. The optical device of claim 41, wherein said absorption edge defined filter edge has a spectral position between UVB and UVA spectral range, said optical thin-film exhibiting a transmission of 1% at the most for light of 315 nm, further exhibiting for light of 340 nm, according to the maximum of a direct pigmenting curve, a transmission of 40% at minimum.

47. The optical device of claim 46, wherein said minimum percentage is 42%.

48. The optical device according to claim 46, wherein transmission for light of 450 nm is 15% at the most.

49. The optical device of claim 48, wherein said transmission is 12% at the most.

50. The optical device of claim 46, wherein transmission for light with wavelengths longer than 450 nm is 15% at maximum or even 12% at maximum, up to light with a wavelength of 900 nm.

51. The optical device of claim 41, wherein said absorption edge defines for 10% transmission at the most for light with a wavelength of 315 nm.

52. The optical device of claim 51, wherein said absorption edge defines for a transmission of 8% at the most for light of 315 nm wavelength.

53. The optical device of claim 51, wherein transmission for light in the UVA spectral range is 85% at minimum.

54. The optical device of claim 53, wherein said transmission for light in the UVA spectral range is 88% at minimum.

55. The optical device of claim 54, wherein said transmission for light in the UVA spectral range is 89% at minimum.

56. The optical device of claim 53, wherein said light in the UVA spectral range has a wavelength of 370 nm.

57. The device of claim 53, wherein said light in the UVA spectral range has a wavelength below 400 nm.

58. A sun-tanner apparatus comprising an optical filter device between ultraviolet source and optical output for tanning, said optical filter device comprising an optical band-pass filter transmitting light in the UVA range and blocking light in the UVB range and in the visible and/or near infrared spectral range, its filter edge between UVB and UVA spectral range being realized by the material inherent absorption edge of the material of a thin-film of an interference filter, the filter edge towards larger wave-length being realized by said interference filter.

* * * * *